United States Patent [19]

Pluta et al.

[11] Patent Number: 5,371,054
[45] Date of Patent: Dec. 6, 1994

[54] COMPOSITIONS FOR USE AS DIAGNOSTIC ANIMAL LITTER AND METHODS FOR THEIR PREPARATION

[75] Inventors: Richard C. Pluta, Clark; Frank J. Washabaugh, Ringoes; William S. Stoy, Princeton, all of N.J.

[73] Assignee: Engelhard Corporation, Iselin, N.J.

[21] Appl. No.: 106,161

[22] Filed: Aug. 13, 1993

[51] Int. Cl.$^5$ .................. B01J 20/12; B01J 21/16
[52] U.S. Cl. ............................. 502/62; 119/173
[58] Field of Search ....................... 502/62; 119/173

[56] References Cited

U.S. PATENT DOCUMENTS

| | | | |
|---|---|---|---|
| 3,059,615 | 10/1962 | Kuceski et al. | 119/1 |
| 3,978,818 | 9/1976 | Heldenbrand | 119/1 |
| 4,020,156 | 4/1977 | Murray | 424/76 |
| 4,315,761 | 2/1982 | Larrson | 71/21 |
| 4,458,629 | 7/1984 | Gerber | 119/1 |
| 4,591,581 | 5/1986 | Crampton | 502/407 |
| 4,638,763 | 1/1987 | Greenberg | 119/1 |
| 4,685,420 | 8/1987 | Stuart | 119/1 |
| 4,914,066 | 4/1990 | Woodrum | 502/62 |
| 5,000,115 | 3/1991 | Hughes | 119/173 |
| 5,143,023 | 9/1992 | Kuhns | 119/173 |
| 5,267,532 | 12/1993 | Franklin et al. | 119/173 |
| 5,279,259 | 1/1994 | Rice et al. | 119/173 |

FOREIGN PATENT DOCUMENTS 7212897  3/1973  Netherlands .......... 119/173

*Primary Examiner*—Carl F. Dees

[57] ABSTRACT

Disclosed are compositions suitable for use as a litter for the accumulation of animal urine comprised of at least one uncalcined clay substrate, said substrate characterized by having a calcium oxide content of less than about 5% by weight and wherein the clay mineral component of said substrate contains at least about 35% by weight attapulgite, combined with at least one chemical pH indicator which provides a visual indication of pH change.

Also disclosed are processes for making such compositions and to litters using such compositions.

14 Claims, No Drawings

COMPOSITIONS FOR USE AS DIAGNOSTIC ANIMAL LITTER AND METHODS FOR THEIR PREPARATION

BACKGROUND OF THE INVENTION

1. Field of the Invention

This invention relates to novel clay compositions useful as animal litters which assist in the diagnosis of animal health problems, to processes for making such compositions and to litters using such compositions.

2. Description of Related Art

Animal litters have been known for many years. They are employed to absorb animal urine and to disperse animal feces until the litter is either cleaned or disposed of.

In the home and veterinary hospital, litters are frequently employed for cats, small dogs, guinea pigs, rabbits, mice, gerbils, etc. It is neither desirable nor economical to constantly dispose of litter when it becomes contaminated with the animal urine or feces which it is meant to contain. Rather, the feces is scooped from the litter employing a litter sieving spoon.

The sieving-cleaning operation is more effective if the litter when contacted by the urine absorbs the urine and forms a deposit or clump of sufficient size and strength to be removed by the sieving-spoon along with the feces.

It is also desirable to include other materials such as bactericides, ammonia binding agents, extenders for such agents and pH indicators.

The addition of pH indicators is particularly useful for a variety of purposes such as to indicate the necessity of removing soiled litter and to provide by the indicated colors of the areas wetted by animal urine information about the health of the animal using the litter. For example, U.S. Pat. No. 5,143,023 which describes a litter for the accumulation of animal urine, such as domestic and cat litter, having at least one visual indicator chemically bound to the litter base material and a method for making such a litter. This patent describes the litter as having the chemical indicator chemically absorbed thereon, rather than merely physically absorbed, permitting the litter to be used as an effective mechanism by animal owners to determine potential health problems with their animals and the same litter may also serve as a useful diagnostic tool in a subsequent visit to a veterinarian. The litter base material is described as having the ability to exchange ions. Compounds to facilitate the agglomeration or clumping of the litter when contacting urine may also be added to litter base material.

There is still need, however, for improved litters having stronger and sharper color indications over the desired pH range, stronger color and sharper contrast as compared to clay substrate, improved color stability and effective agglomeration or clumping. It is also desirable that the initial color of a soiled litter be capable of reconstitution after the initial color has faded. It is, therefore, the purpose of the invention described herein to provide improved animal litters with such desired properties.

SUMMARY OF THE INVENTION

This invention relates to compositions and their use as litter for the accumulation of animal urine and to processes for preparing such compositions.

In one embodiment, this invention relates to a composition suitable for use as a litter for the accumulation of animal urine comprised of at least one uncalcined clay substrate, said substrate characterized by having a calcium oxide content of less than about 5% by weight and wherein the clay mineral component of said substrate has a attapulgite content of at least about 35% by weight, in combination with at least one chemical pH indicator.

In a further embodiment, this invention relates to a method for preparing said composition comprising the steps of (i) selecting an uncalcined clay substrate, said substrate characterized by having a calcium oxide content of less than about 5% by weight and wherein the clay mineral component of said substrate has an attapulgite content of at least 35% by weight; and (ii) when the free-moisture content of the clay substrate selected in step (i) has a moisture content greater than 20% by weight, drying said clay substrate such that said substrate has a free-moisture content of about 20% by weight or less; (iii) fractionating said clay substrate such that the substrate is within an 8/60 mesh screen (U.S. standard) particle size distribution; (iv) applying to said fractionated clay substrate an indicator composition comprised of at least one chemical pH indicator.

DESCRIPTION OF THE PREFERRED EMBODIMENT

As previously stated, the compositions of this invention are comprised of uncalcined clay substrates having a CaO content of less than about 5% by weight and wherein the clay mineral component of said substrate has an attapulgite content of at least about 35% by weight.

Clay materials useful in making compositions of the instant invention include those obtained from the Meigs-Attapulgus-Quincy fullers earth district, located in south-west Georgia and northern Florida. In the southern portion of this district, in the vicinity of Attapulgus, Ga., the fullers earth ore horizons consist predominantly of clay mineral palygorskite, and contain minor amounts of smectite and the non-clay minerals of quartz, dolomite, calcite, phosphate pellets, feldspars and various heavy minerals. In the northern portion of the district, in the vicinity of Meigs, Ga., the predominate clay mineral phases are smectite and palygorskite with lesser amounts of sepiolite and kaolinite. Non-clay phases include quartz, feldspar, calcite, dolomite, and a variety of heavy minerals. Diatoms are abundant. While highly variable, the Meigs deposits appear to be layered, with smectite and kaolinite predominating in the near surface environment with palygorskite content increasing with depth.

For purposes herein the term attapulgite is used to mean chain lattice type clay minerals, encompassing minerals and mineral groups variously referred to in the literature as attapulgite, palygorskite, sepiolite and hormite.

Those skilled in the art will be familiar with methods to determine the relative amounts of various mineral phases present in such clays. X-ray diffraction techniques can be employed for qualitative determination of the mineral phases present and may be sufficient for determination of single mineral assemblages. However, XRD does not yield highly accurate numerical estimates on more complex geological materials, such as the variable clay assemblages of the Meigs deposit. Other methods, such as comparing the chemical analyses of the unknown samples with the analyses of known, purified clay mineral components are also useful.

The clays suitable for use in the practice of this invention have a clay mineral component which contains at least about 35% by weight attapulgite; preferably at least about 50% by weight attapulgite. The clay mineral component of the clay substrates suitable for use in this invention is typically at least 50% by weight of the clay substrate material; preferably at least about 70% by weight.

The clay substrates useful for the purposes of this invention are uncalcined. Uncalcined clays contain structural water that is held chemically in the molecular structure of the clay and as used herein shall mean those clays wherein the structural water has not been substantially affected. Typically, this means that the clay has not been heated to above about 500° F.; preferably not more than 400° F.

The clays suitable for use in this invention also have a calcium oxide content, calculated on a volatile-free basis, of less than about 5% by weight and preferably less than about 4% by weight. As used herein "volatile-free" refers to a composition which is free of those components removed by heating such composition to constant weight at 1800° F. A calculation on a volatile-free basis is where the analysis of a particular chemical component (e.g., CaO, MgO, etc.) of a composition is adjusted to deduct volatile constituents of said composition from the basis of the calculation.

In another preferred embodiment, the free-moisture content of the clay substrate is preferably from about 5% up to about 20% by weight, more preferably from about 10% up to about 20% by weight. As used herein, the term "free-moisture" content refers to the amount of water which is loosely held by the clay substrate, rather than chemically combined water which is an integral part of the crystal lattice of the substrate. As used herein, the "free-moisture content" is the amount of water removed from the clay by heating to constant weight at 220° F. Typically, the substrate as mined contains up to about 45% by weight free-moisture content. When the free-moisture content of the clay substrate selected is greater than about 20% by weight, the clay substrate is preferably dried to the desired free-moisture content by heating the clay to a temperature of less than about 400° F., more preferably 250° F. until the desired moisture content is attained.

The clay substrate is then fractionated so that the particle size is not so large as to allow urine to pass through the litter material to the bottom of the litter or to cause discomfort the animal's paws, but not so small as to be dusty when handled or result in tracking of the clay by the animal's feet. Furthermore, the clay substrate is sized to provide effective clumping. Therefore, the clay substrates useful in this invention should typically have few particles that are coarser than 8 mesh (U.S. Standard). Furthermore, useful substrates should typically have few particles that are finer than 60 mesh (U.S. Standard). Preferably, the clay substrates used herein have a particle size distribution within a range such that substantially few of the particles are coarser than 8 mesh (U.S. Standard) or finer than a 60 mesh (U.S. Standard); the particle size distribution within this preferred range is not critical. For the purposes of brevity, particle size distribution ranges are referred to by the maximum/minimum particles sizes discussed hereinabove (U.S. Standard), e.g., 8/60 mesh. For example, an 8/60 particle size distribution means that substantially all of the particles pass through an 8 mesh screen (U.S. Standard) whereas substantially all of the particles will not pass through a 60 mesh screen (U.S. Standard). In a useful embodiment, the clay substrate has a particle size distribution of 12/50 mesh. In another useful embodiment, the clay substrate has a particle size distribution of 8/30 mesh. The particle sizes used herein are determined by standard methods known to those of ordinary skill in the art.

The clay substrates of this invention are combined with a chemical pH indicator which provides a visual indication of pH change. The pH indicator useful for the purposes of this invention may be any indicator which changes color over a pH range of from about 3 up to about 10, preferably from about 5 up to about 9. The choice of indicator will depend on desired end use. For example, an indicator that changes color in the pH range between pH 7 and pH 8 can be used for a clumping cat litter by the typical cat owner. This gives the owner an early warning of the onset of urinary tract problems including Feline Urological Syndrome (FUS) also known as feline lower urinary tract disease (LUTD). Other dyes can be used on products for veterinarians as a more precise indicator of urine pH. Such dyes include bromocresol purple which yields progressive color variation over the pH range of 5 to 9. This enables veterinarians to more accurately determine the pH level of an animal's urinary discharge. Other dyes can be selected to predict levels of glucose, ketones, bilirubin, urobilinogen, and protein. Diseases such as nephropathy and renal amyloidosis can be determined with such dye utilization.

The chemical indicator may include, but is not limited to, bromthymol blue (dibromothymolsulfonphthalein), phenol red (phenolsulfonphthalein), cresol red (o-cresolsulfonphthalein), bromcresol purple (dibromo-o-cresolsulfonphthalein), p-bromobenzenesulfonyl chloride, Congo red (diphenyldiazo-bis-1-naphthylamine-4-sodium sulfonate), methyl orange (sodium salt of dimethylaminoazobenzenesulfonic acid), bromchlorphenol blue (dibromodichlorophenolsulfonphthalein), P-ethoxychrysoidine (4'-ethoxy-2,4-diaminoazobenzene), naphthyl red (naphthylaminoazobenzene), bromcresol green (tetrabromo-m-cresolsulfonphthalein), methyl red (dimethylaminoazobenzene-P-carboxylic acid), lacmoid, litmus, chlorphenol red (dichlorophenolsulfonphthalein), benzoyl suramine G, azolitmin, bromphenol red (dibromophenolsulfonphthalein), dibromophenoltetrabromophenosulfonphthalein, neutral red (amino-dimethylamino-toluphenalin-hydrochloride), rosolic acid aurin (corallin), quinoline blue (cyanine), a-naphthlophthalein, metacresol purple (m-cresolsulfonphthalein), ethyl bis-[2,4-dinitrophenyl] acetate, Tropeolin 000 (a-Naphtol orange, a-naphthlolazobenzenepsulfonic acid), thymol blue (thymolsulfonphthalein), o-cresolphthalein, thymolphthalein, Nile blue (aminodiethylaminonaphthophenazoxoniumchloride). Curcumin (Brilliant yellow, sulfanilic acid-azodiphenylaminosulfonic acid), dimethylaminoazobenzene (dimethyl yellow, methyl yellow, butter yellow), Metanil yellow (Victoria yellow, Metanil extra, Tropeolin G, sodium salt of diphenylaminoazo-m-benzenesulfonic acid), Methyl Violet 6B (pentamethylbenzylpararosaniline-hydrochloride), p-Naphtholbenzene, Resazurin, Tropeolin 00 (Orange IV, Aniline Yellow, Diphenyl Orange, sodium salt of diphenylaminoazo-p-benzenesulfonic acid), xylenol blue (p-xylenonlsulfonephthalein) and mixtures thereof.

The various chemical pH indicators, also referred to herein as "dyes," can be used in combination with the clay substrates of this invention in their acid, neutral (anhydride) or salt forms. Bromothymol blue, phenol red and bromocresol purple are preferred dyes. Mixtures of two or more dyes may be used but non-mixtures (single dye) are preferred. The dye is typically applied to the clay substrates of this invention as a solution (including dispersions, suspensions, etc.). Solvents useful for this purpose include water and organic solvents such as alcohols and ketones; preferred organic solvents are those which are water miscible. In the case of acid or neutral indicators, it is preferable to form a concentrate of said indicator in a non-aqueous, water miscible solvent, such as ethanol, methanol and acetone, which is then mixed with water for application to said clay substrate. With salt forms of the dyes, the solvent is water. The preferred salt form of the dyes is the sodium salt. With sodium salt forms of the dyes, solution in water is possible. The acid forms may be solubilized by first making a 0.05–0.10 wt. % solution of sodium hydroxide or sodium carbonate and then adding the acid form to this solution. Dye solutions can be applied to the clay substrates by coating methods, such as spraying, known to those of ordinary skill in the art. A suitable method involves spraying atomized droplets of a dye solution directly onto a cascade of clay particles as the clay particles fall through the spraying chamber. The dyes are typically applied in 0.2–0.5 wt % solutions to the clay substrates. The amount of dye contained in treated clay substrate composition of this invention is preferably from about 0.005% up about to 0.05% by weight of the composition, more preferably from about 0.01% up to about 0.03%.

Dye concentrations in the solution and the amount of solution sprayed onto the clay can be varied in order to control the free-moisture content of the compositions of this invention. The desired free-moisture content of the composition of this invention ranges from about 15% up to about 30% by weight most preferably about 20%.

As previously mentioned, these compositions are particularly useful as litter for the accumulation of animal urine. In addition to providing stronger and sharper color distinctions between pHs over the desired pH range, improved color stability and effective agglomeration, the compositions do not require the addition of (i) binders for agglomeration, (ii) pH pre-adjustment of substrate surface, (iii) heating of dye solutions to achieve solubility of water soluble dyes, or (iv) other additives. The initial colors generated by wetted areas of the compositions of the instant invention may fade and lose color over a period of time (usually hours). However, the initial indicated colors can be reconstituted by wetting the previously wetted area with a few drops of distilled water; an advantageous property of the claimed compositions.

Examples of this invention are included hereinbelow. Of course, these examples are not intended as limiting this invention as modification of the examples by ordinary expedient will be readily apparent to those of ordinary skill in the art.

Unless otherwise indicated in the following examples and elsewhere in the specification and claims, all parts and percentages are by weight, temperatures are in degrees Fahrenheit and pressures are at or near atmospheric.

The method employed herein to calculate the attapulgite content of the clay mineral component of the clay substrates used in the examples (also useful for any unknown clays sampled from the Attapulgus-Meigs fullers earth district) compares the chemical analysis, specifically the $Al_2O_3/MgO$ ratio, of the samples with that of published, purified natural samples of attapulgite and smectite minerals. This is referred to as the chemical ratio calculation method. For purposes of these examples, this calculation is based on the clay mineral component consisting of only attapulgite and smectite minerals; the presence of minor amounts of other clay minerals such as kaolinite has only a minor effect on this calculation. The measured chemical analyses of the purified samples of attapulgite and smectite minerals used herein are published in U.S. Pat. No. 3,477,566 (attapulgite) and by Weaver and Pollard, 1973, *The Chemistry of Clay Minerals* (average of 101 Montmorillonite and beidellite samples). The chemical analyses from these references are recalculated on a volatile free basis ("VFB") and the $Al_2O_3/MgO$ ratio is calculated, as reported below:

| | Purified Compositions (VFB) | | | |
|---|---|---|---|---|
| | CaO | MgO | $Al_2O_3$ | $Al_2O_3/MgO$ |
| Attapulgite | 0.35 | 15.89 | 9.35 | 0.59 |
| Smectite | 1.27 | 3.85 | 23.77 | 6.18 |

Since a portion of the MgO content as measured by chemical analysis of the unknown samples is considered to be contained in non-clay minerals, particularly Mg-carbonates such as dolomite, an adjustment is made to account for such carbonate contents in the non-clay component of the samples, as is described below.

STEPS OF THE CALCULATION

Step 1

The fullers earth clay sample is analyzed by well-known X-ray fluorescence (XRF) techniques, and the reported oxide contents of CaO, MgO, $Na_2O$, $K_2O$, $Fe_2O_3$, $TiO_2$, $P_2O_5$, $SiO_2$, $Al_2O_3$ are recalculated on a volatile-free basis.

Step 2

Based on the referenced purified mineral compositions a 50/50 mixture of attapulgite/smectite contains 0.81 units of CaO. An unknown sample with a CaO content (VFB) substantially in excess of this amount indicates the presence of carbonate minerals in the sample. In the examples below, Clay II and Clay III are indicated as having carbonate minerals. To account for this, 0.81 units CaO is deducted from the CaO (VFB) content of these samples to yield a residual CaO content, which is considered to be contained in carbonate minerals.

Step 3

The residual CaO content is considered to be contained in dolomite and calcite. If all the residual CaO is in dolomite, the amount of MgO contained in dolomite is calculated as: (residual CaO/0.40) * 0.29 = MgO units in dolomite since the weight percent of CaO in dolomite is 40%, and the weight percent of MgO in dolomite is 29%. The calculated MgO units in dolomite are deducted from MgO units (VFB) of the sample to determine MgO units available for clay component minerals. If all residual CaO is contained in calcite, MgO units available for clay component minerals is equal to MgO units (VFB).

Step 4

The process of Step 3 results in two estimates of MgO contained in the clay component minerals (calcite case, dolomite case). These two MgO unit values are then used to calculate two values for the ratio $Al_2O_3/MgO$ for the unknown sample. The resultant ratios are then compared to the $Al_2O_3/MgO$ ratios of the pure compositions above, and the attapulgite content of the clay mineral component is calculated by straight-line interpolation. That is, where x is the $Al_2O_3/MgO$ ratio of the sample:

% attapulgite=(6.18−x)/(6.18−0.59) * 100

In the cases of Clay II and Clay III below, where there is substantial residual CaO, there are two values of x for each sample (calcite case, dolomite case), so the attapulgite content of the clay mineral component is reported as a range. In the case of Clay I and Clay IV, where residual CaO is low, the difference in the calculated attapulgite content between the dolomite case and calcite case is small, and attapulgite content of the clay mineral component is reported as a single calculated value.

The general procedure for the preparation of the clay substrates used in the examples provided herein is as follows:
The crude clay is crushed to pass through a 0.28 inch screen. The sized fraction is dried such that the bed of clay material attains a maximum temperature of about 250° F. The dried clay material is then milled and sieved by wire mesh screens with the 12/50 mesh fraction recovered to yield the clay substrates characterized in Table A as follows:

TABLE A

| ANALYSIS OF CLAYS USED IN THE EXAMPLES (CHEMICAL ANALYSIS ON A VOLATILE-FREE BASIS) | | | | |
|---|---|---|---|---|
| | CLAY I | CLAY II | CLAY III | CLAY IV |
| Free Moisture | 13.7 | 13.4 | 9.9 | 20.9 |
| CaO | 1.28 | 3.46 | 9.93 | 0.93 |
| MgO | 4.45 | 11.20 | 8.88 | 2.84 |
| Na$_2$O | 0.29 | 0.06 | 0.07 | — |
| K$_2$O | 1.20 | 0.89 | 0.88 | 1.16 |
| Fe$_2$O$_3$ | 4.40 | 3.70 | 3.19 | 5.22 |
| TiO$_2$ | 0.57 | 0.48 | 0.47 | 0.71 |
| P$_2$O$_5$ | 0.67 | 1.95 | 0.98 | 0.16 |
| SiO$_2$ | 72.60 | 67.20 | 63.00 | 73.6 |
| Al$_2$O$_3$ | 13.00 | 9.93 | 10.00 | 15.39 |

Clay I from a clay pit located near Meigs, Ga. XRD analysis indicates that the clay contains attapulgite, smectite, quartz, and minor calcite and dolomite. Using the chemical ratio calculation method described herein, the clay mineral component of Clay I is calculated to contain about 58% by weight attapulgite.

Clay II is from an Engelhard Corporation mine located near Attapulgus, Ga. XRD analysis indicates that the clay substrate material contains attapulgite, smectite, quartz, calcite and dolomite. The clay mineral component of the substrate material is calculated by the chemical ratio calculation method to be about 93-95% attapulgite.

Clay III is from the same location as Clay II. The clay mineral component is calculated by the chemical ratio method to be 85-90% attapulgite.

Clay IV is from the same mine as Clay I. Clay IV is from a clay horizon stratigraphically higher (closer to the surface) than Clay I. The clay mineral component of Clay IV is calculated by the chemical ratio method to be about 13% by weight attapulgite.

EXAMPLE 1

A sample of Clay I is treated with a dye solution of Bromocresol purple dye in the free acid form added to a 20:1 de-ionized water to ethanol solution. The dye (3.5 parts) is first allowed to dissolve by stirring in 50 parts of ethanol. This solution is then added to 950 parts deionized water and stirred until a uniform mixture results. This solution (150 parts) is sprayed on 2000 parts of Clay I under agitation using a high intensity mixer. The resulting treated Clay I contains 0.024% by weight Bromocresol purple dye. The color of the treated Clay I is light yellow.

EXAMPLE 2

A sample of Clay II is treated with a dye solution of phenol red in the sodium salt form. The sodium salt of phenol red (3.5 parts) is added to 1000 parts deionized water and stirred until all the dye is solubilized. This solution (150 parts) is sprayed on 2000 parts of Clay II under agitation using a high intensity mixer. The resulting treated Clay II contains 0.024% by weight of the sodium salt of phenol red. The color of the treated Clay II is light pink.

EXAMPLE 3

A sample of Clay III is treated in accordance with the procedure of Example 2. The color of treated Clay III is dark pink.

EXAMPLE 4

A sample of Clay IV is treated in accordance with the procedure of Example 2 using the sodium salt form of bromocresol purple in place of the sodium salt of phenol red. The color of this treated Clay IV is brown.

EXAMPLE 5

A sample of Clay IV is treated in accordance with the procedure of Example 1. The color of this treated Clay IV is light brown.

The following procedure is used to test the materials prepared according to the foregoing examples and the results of such tests are summarized in Table B below. The materials are tested for use as cat litter using buffered solutions that cover the typical pH range of feline urine, i.e., solutions of pH 5.00, 7.00 and 8.00, (commercially available from Aqua Solutions). The material is prepared as a strip having a depth of about one inch, a width of about two inches and a length of about six inches spread out on a flat surface. To this strip about 3 ml of each pH-buffered solution is applied to three separate areas of the strip to form circular areas each about one and one-half inches in diameter. These solution wetted areas are observed for color change in terms of contrast with the surrounding dry areas for both intensity of color (chroma) and hue. As in Litmus paper, these colors should reflect the appropriate pH levels. These freshly developed colors are observed for their resistance to change (reversion).

TABLE B

COLOR ANALYSIS OF EXAMPLES

| Example | | Initial Indication | 8 Hr. Indication |
|---|---|---|---|
| 1 | pH 5 | Bright yellow | Bright yellow |
|   | pH 7 | Bright blue | Bright blue |
|   | pH 8 | Bright purple | Bright purple |
| 2 | pH 5 | Bright yellow | Bright yellow, 0.5 mm reverted ring |
|   | pH 7 | Dull yellow | Dull yellow, 0.5 mm reverted ring |
|   | pH 8 | Bright red | Bright red |
| 3 | pH 5 | *Bright yellow reverted ring | Bright red |
|   | pH 7 | *Dull yellow, reverted ring | Bright red |
|   | pH 8 | Bright red | Bright red |
| 4 | pH 5 | **Bright yellow | No distinct color, reverted to brown |
|   | pH 7 | **Bright blue | No distinct color, reverted to brown |
|   | pH 8 | **Bright purple | No distinct color, reverted to brown |
| 5 | pH 5 | **Bright yellow | No distinct color, reverted to brown |
|   | pH 7 | **Bright blue | No distinct color, reverted to brown |
|   | pH 8 | **Bright purple | No distinct color, reverted to brown |

*Initial indication - the colors began changing within minutes.
**Complete color loss occurred within 3 to 5 minutes.

Examples 1 and 2, products of the instant invention, provide excellent color discrimination between pH the levels and stability after eight hours, whereas comparative Examples 3, 4, and 5 fail to provide the color stability of the instant invention.

What is claimed:

1. A composition suitable for use as a litter for the accumulation of animal urine comprised of at least one uncalcined clay substrate, said substrate characterized by having a CaO content of less than about 5% by weight and wherein the clay mineral component of said substrate has an attapulgite content of at least about 35% by weight, in combination with at least one chemical pH indicator.

2. A composition according to claim 1, wherein the attapulgite content of the clay mineral component of said clay substrate is at least about 50% by weight.

3. A composition according to claim 1 wherein the CaO content of said clay substrate is less than about 4% by weight of the clay substrate.

4. A composition according to claim 1 wherein the free-moisture content of said clay substrate is from about 5% up to about 20% by weight of the clay substrate.

5. A composition according to claim 1 wherein the free-moisture content of said composition is from about 15% up to about 30% by weight of said composition.

6. A composition according to claim 1 wherein said indicator is in the salt form.

7. A composition according to claim 1 wherein said indicator in the acid form.

8. A composition according to claim 1 wherein a single chemical pH indicator is present.

9. A composition according to claim 1 wherein said indicator changes color over the pH range of about 5 up to about 9.

10. The composition of claim 1 wherein said clay substrate has a particle size distribution within 8/60 mesh.

11. A litter for the accumulation of animal urine comprising the composition of claim 1.

12. A method for preparing the composition of claim 1 comprising the steps of:
    i) selecting at least one uncalcined clay substrate, which is characterized by having a CaO content of less than about 5% by weight and wherein the clay mineral component of said substrate contains at least about 35% by weight attapulgite;
    ii) when the free-moisture content of the clay substrate selected in step (i) is greater than 20% by weight, drying said clay substrate such that said substrate has a free-moisture content of about 20% by weight or less;
    iii) fractionating said clay substrate such that the substrate is within a 8/60 mesh screen (U.S. Standard) particle size distribution;
    iv) applying to said fractionated clay substrate an indicator composition comprising at least one chemical pH indicator.

13. The method of claim 12 wherein said indicator composition is applied to the surface of said clay substrate by spraying.

14. The method of claim 12 wherein the indicator composition comprises a single chemical pH indicator.

* * * * *